United States Patent

Propp

[11] Patent Number: 6,123,683
[45] Date of Patent: Sep. 26, 2000

[54] PILL DELIVERY APPARATUS

[75] Inventor: Donald J. Propp, Dewitt, Mich.

[73] Assignee: Tri-State Hospital Supply Corporation, Howell, Mich.

[21] Appl. No.: 09/337,922

[22] Filed: Jun. 22, 1999

[51] Int. Cl.⁷ .................................................. A61M 31/00
[52] U.S. Cl. ................................................................ 604/60
[58] Field of Search ................................ 604/10, 14, 15, 604/27, 28, 36, 38, 514, 57, 59, 60, 164, 311

[56] References Cited

U.S. PATENT DOCUMENTS

| | | | |
|---|---|---|---|
| 400,056 | 3/1889 | Christy | 604/36 |
| 3,042,030 | 7/1962 | Read | 604/59 |
| 3,297,031 | 1/1967 | Bray | 604/60 |
| 3,757,781 | 9/1973 | Smart | 604/60 |
| 4,060,083 | 11/1977 | Hanson | 604/60 |
| 4,645,488 | 2/1987 | Matukas | 604/59 |
| 4,753,636 | 6/1988 | Free | 604/49 |
| 4,792,333 | 12/1988 | Kidder | 604/83 |
| 4,900,303 | 2/1990 | Lemelson | 604/54 |
| 4,936,827 | 6/1990 | Grimm et al. | 604/60 |
| 5,584,805 | 12/1996 | Sutton | 604/60 |
| 5,649,906 | 7/1997 | Gory et al. | 604/53 |
| 5,788,664 | 8/1998 | Scalise | 604/15 |

Primary Examiner—Sharon Kennedy
Attorney, Agent, or Firm—Fildes & Outland, P.C.

[57] ABSTRACT

A pill delivery apparatus for administering pills or parts thereof into a body cavity. The apparatus includes a flexible conduit having a grasping end and a delivery end. The delivery end releasably holds a pill to be administered into the body cavity. A slide wire is disposed within the conduit for slidable movement therein. The slide wire has a ramming end adjacent the delivery end. The slide wire also has a handle end extending beyond the grasping end of the flexible conduit. The pill is loaded into the delivery end of the conduit when the ramming end is moved away from the delivery end. The pill is unloaded into the body cavity by moving the slide wire until the ramming end engages the pill and forces the pill out of the conduit.

12 Claims, 2 Drawing Sheets

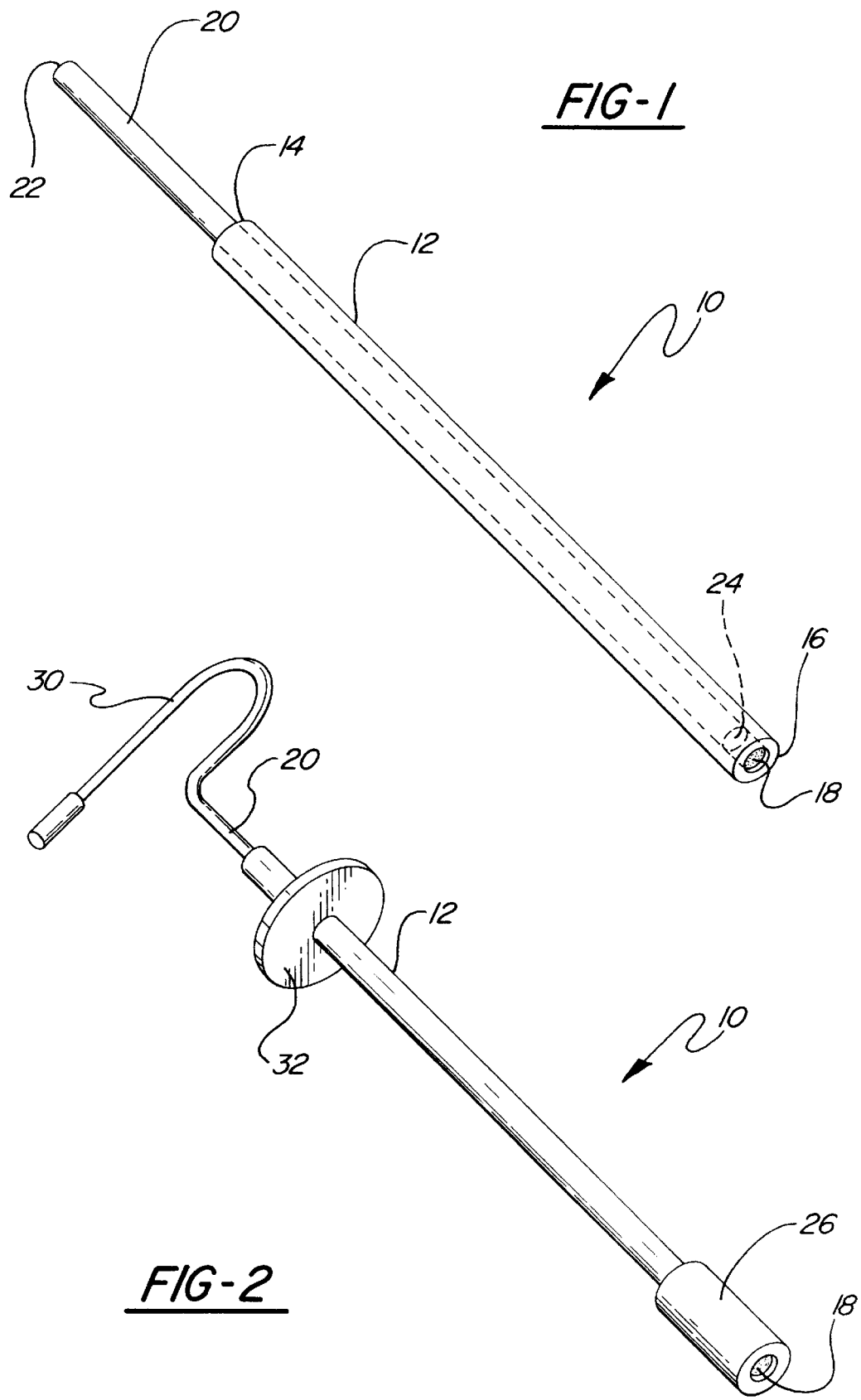

PILL DELIVERY APPARATUS

FIELD OF THE INVENTION

This invention relates to applicators for introducing medicine into a body cavity and, more particularly, to an apparatus for administering pills or parts thereof into a body cavity.

BACKGROUND OF THE INVENTION

It is known in the art relating to medicine applicators to provide a disposable applicator for facilitating the injection of gel-like medicine into a vagina for treating vaginal yeast infections and the like. It is not known of any applicators that facilitate the injection of pills or parts thereof into a body cavity. For example, a pill or parts thereof used to ripen the cervix and induce labor is inserted directly by a nurse or doctor into the vagina or cervical opening with their fingers.

Several disadvantages are associated with this method of application. Because of the pressure of the fetus and placenta on the vaginal wall, it is very difficult for the nurse or doctor to hold the pill on the end of one, or between two fingers, and at the same time insert fingers far enough into the vagina to reach posterior fornix without the pill slipping out of the finger(s) too early. It is often unknown exactly where the pill is disposed. For example, the pill is sometimes still stuck on the perinatal nurse's finger(s) or gloves when the nurse removes finger(s) from the vagina. This uncertainty of placement can have adverse consequences on the progress of cervical ripening and labor induction. Also, the insertion of the fingers into the vagina may cause excessive stretching trauma. Therefore, it is desirable to provide an apparatus that will facilitate the introduction of pills or parts thereof into a body cavity, such as a vagina.

SUMMARY OF THE INVENTION

The present invention provides a pill delivery apparatus for administering pills or parts thereof into a body cavity. The apparatus includes a flexible conduit having a grasping end and a delivery end. The delivery end releasably holds a pill to be administered into the body cavity. The user holds the grasping end while placing the delivery end of the conduit into the body cavity. A slide wire is disposed in the conduit for slidable movement therein. The slide wire has a ramming end and a handle end. The ramming end is adjacent the delivery end of the conduit. The handle end extends beyond the grasping end of the conduit to allow the wire to be held and then pushed through the conduit by the user toward the delivery end to unload the pill into the cavity.

In one embodiment, a flexible sleeve is attached to the delivery end of the conduit to form a pill holder. The sleeve is made from a resilient material. The sleeve expands to allow the insertion of the pill. Once the pill is inserted, the sleeve contracts around the pill, holding it in place.

A ramming head element is attached to the ramming end of the wire and is located in the sleeve. The outer diameter of the head element is greater than the inner diameter of the conduit. The outer end of the head element provides a ramming surface to push the pill out of the sleeve. The wire end of the ramming head element hits the end of the conduit and stops the wire and head element from being completely pulled out of the conduit during pill loading.

In another embodiment, a handle extends from the handle end of the slide wire. The handle is configured to ensure that the slide wire is pushed through the conduit for a predetermined distance. The predetermined distance is equal to the amount of movement needed to unload the pill from the sleeve of the apparatus, thus ensuring that the pill has been unloaded before removal of apparatus from the body cavity. The handle increases the ease with which the user is able to hold the apparatus and move the wire to load and unload the pill. A finger flange is provided on the outer diameter of the conduit about the grasping end of the conduit to allow the nurse to unload the pill with one hand without the assistance of a second person.

A pill or parts thereof are administered into the body cavity by loading the pill into the delivery end of the conduit. The flexible conduit is bent into the desired shape to conform to the body cavity. For easier insertion into the body cavity, the outside of the conduit and sleeve may be lubricated. The delivery end of the conduit is placed in the body cavity with one hand and then the slide wire is pushed toward the delivery end with the nurse's other hand. The ramming end engages the pill and forces the pill out of the conduit into the cavity. The conduit and slide wire are then removed from the body cavity. The apparatus provides a non-intrusive method of introducing pills into a body cavity.

These and other features and advantages of the invention will be more fully understood from the following detailed description of the invention taken together with the accompanying drawings.

BRIEF DESCRIPTION OF THE DRAWINGS

In the drawings:

FIG. 1 is a perspective view of a pill delivery apparatus in accordance with the invention;

FIG. 2 is a perspective view of a pill delivery apparatus in accordance with one embodiment of the invention;

DETAILED DESCRIPTION OF THE INVENTION

Figure 3:
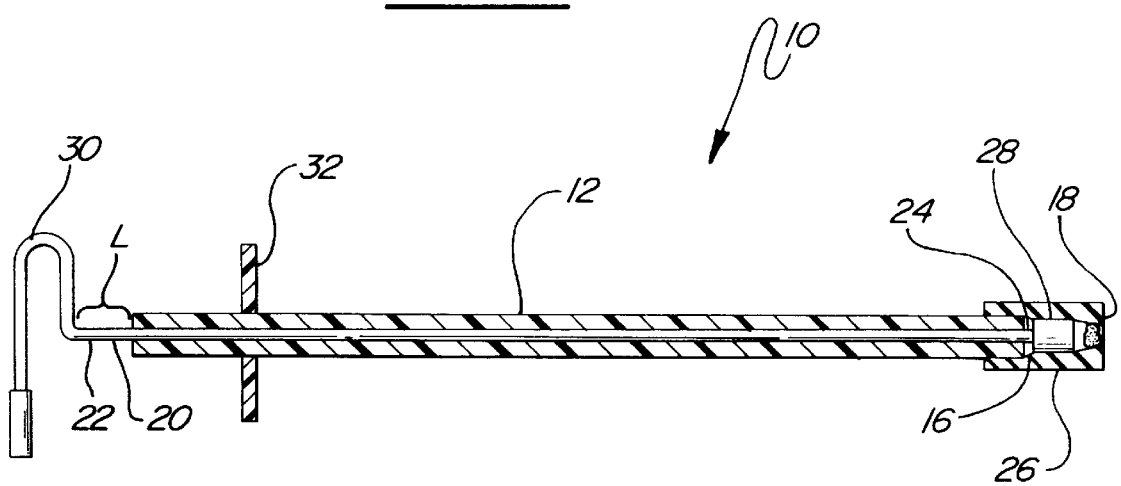
FIG. 3 is a cross-sectional side view of the pill delivery apparatus of FIG. 2 with a pill loaded in a flexible sleeve of the pill delivery apparatus.

Referring now to the drawings in detail, numeral 10 generally indicates a pill delivery apparatus for administering pills or parts thereof into a body cavity. The apparatus 10 provides a non-intrusive method of reliably placing a pill into a body cavity.

FIG. 1 illustrates one embodiment of the pill delivery apparatus 10 having a flexible conduit 12 to be inserted into the body cavity. The conduit 12 has a grasping end 14 and a delivery end 16. The user holds grasping end 14 while inserting conduit 12 into the body cavity. Delivery end 16 releasably holds a pill 18 to be administered. The conduit 12 is made from a flexible material so that the conduit 12 may be conformed to follow the contours of the body cavity, such as a vagina. Bending of the conduit 12 provides non-intrusive access to the body cavity.

A slide wire 20 is disposed in the conduit 12. The slide wire 20 longitudinally moves within the conduit 12. The slide wire 20 has a handle end 22 and a ramming end 24. The user holds the handle end 22 while pushing or pulling the wire 20 through the conduit 12 to unload or load the pill 18. The pill 18 is loaded into the delivery end 16 when the slide wire 20 is pulled away from the delivery end 16. When the wire 20 is pushed toward the delivery end 16 of the conduit 12, the ramming end 24 engages the pill 18 and forces it out of the conduit 12 into the body cavity. The wire 20 is flexible and bends with the conduit 12.

In another embodiment of the present invention, illustrated in FIGS. 2 and 3, a flexible sleeve 26 is attached to the delivery end 16 of the conduit 12 to form a pill holder. The sleeve 26 is made from a resilient material, such as rubber. The sleeve expands to allow the insertion of the pill 18. Once the pill 18 is inserted, the sleeve contracts around the pill 18, holding it in place. An adhesive may be used to attach the sleeve 26 to the conduit 12. Alternatively, a friction interface fit may be used to attach the sleeve 26 over the conduit 12.

A ramming head element 28 is attached to the ramming end 24 of the slide wire 20. In this embodiment, the slide wire 20 extends beyond the delivery end 16 of the conduit 12 and the head element 28 is located in the flexible sleeve 26. The outer diameter of the head element 28 is greater than the inner diameter of the conduit 12 to provide a larger ramming surface to engage the pill and to prevent the wire 20 from being completely removed from the conduit 12.

A handle 30 extends from the handle end 22 of the slide wire 20 to allow one person handling of the apparatus 10. The handle 30 is configured to allow the wire 20 to be pushed through the conduit 12 a predetermined distance, L. The predetermined distance, L, equals the amount of movement needed to unload the pill 18 from the conduit 12. This construction ensures that the pill 18 has been ejected from the conduit 12 before removing the apparatus 10 from the body cavity. A finger flange 32 is provided on the outer diameter of the conduit 12 about the grasping end 14 of the conduit 12 to allow the nurse to unload the pill with one hand without the assistance of a second person. The nurse places her index and ring fingers on the finger flange 32 and pushes the handle 30 toward the delivery end using the thumb.

A pill or parts thereof are administered into the body cavity by loading the pill 18 into the delivery end 16 of the conduit 12. The flexible conduit 12 is bent into the desired shape to conform to the body cavity. The outside of the conduit 12 may be lubricated for easier insertion. The conduit 12 is placed in the body cavity and then the slide wire 20 is pushed toward the delivery end 16 of the conduit 12. The ramming end 24 engages the pill 18 and forces the pill 18 out of the conduit 12 into the cavity. The apparatus 10 is then removed from the body cavity. The apparatus 10 facilitates the introduction of medicine into the body cavity.

Figure 4:
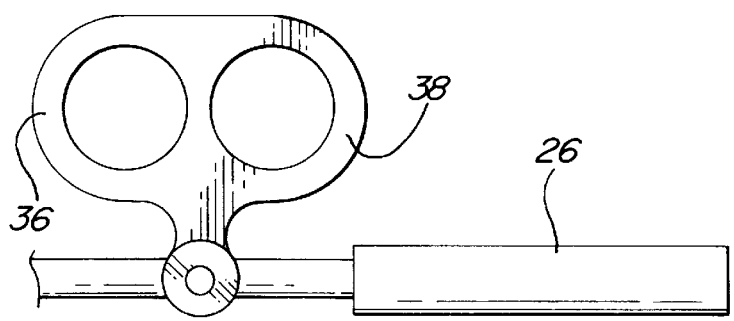
FIG. 4 is a perspective view of a pill delivery apparatus of FIG. 2 with a retaining member having two circularly shaped finger-receiving portions.
Figure 5:
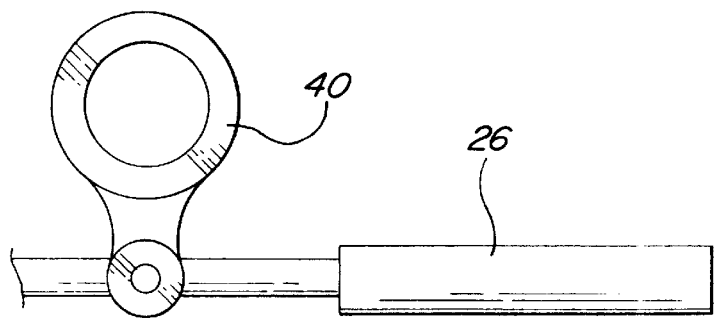
FIG. 5 is a perspective view of a pill delivery apparatus of FIG. 2 with a retaining member having one circularly shaped finger-receiving portion.
Figure 6:
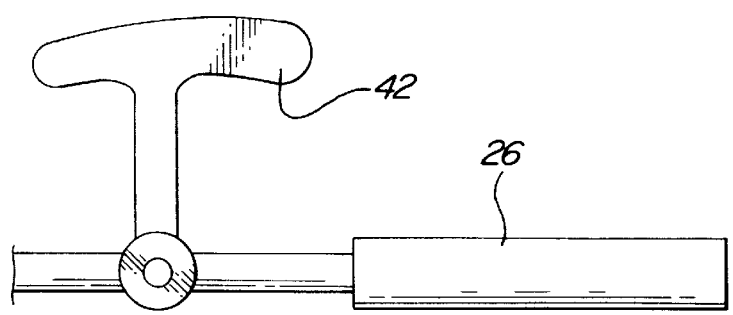
FIG. 6 is a perspective view of a pill delivery apparatus of FIG. 2 with a retaining member having a tee shaped finger-receiving portion.

A finger retaining member 34 is mounted on the outer diameter of the conduit 12 adjacent the flexible sleeve 26 to keep fingers close to the delivery end 16, guiding the insertion of the conduit 12 into the body cavity. The retaining member 34 may be made from a soft resilient material to stretch over various sized fingers and to provide a low profile so as not to drag on the vaginal walls. The retaining member 34 may consist of two circularly shaped finger-receiving portions 36, 38 as shown in FIG. 4, one circularly shaped finger-receiving portion 40 as shown in FIG. 5 or a tee shaped finger-receiving portion 42 as shown in FIG. 6.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A pill delivery apparatus for administering pills or parts thereof into a body cavity, said apparatus comprising:

a flexible conduit having grasping and delivery ends;

a flexible sleeve attached to the delivery end of the conduit to define a pill holder;

said delivery end releasably holding a pill to be administered into the body cavity;

a slide wire disposed in said conduit for slidable movement therein;

said slide wire having a ramming end adjacent said pill holder and a handle end extending beyond the grasping end of said flexible conduit; and a ramming head element having a greater outer diameter than the inner diameter of the flexible conduit coupled to the ramming end of the wire;

whereby the pill is loaded into said delivery end when said ramming end moved away from said delivery end, and the pill is unloaded from said delivery end by moving said slide wire toward the delivery end to engage the pill with said ramming end.

2. An apparatus of claim 1 wherein the slide wire includes a handle extending from said handle end of the wire.

3. An apparatus of claim 2 wherein the configuration of the handle is adapted to ensure that the wire is pushed through the conduit for a predetermined distance.

4. An apparatus of claim 1 further including a finger flange mounted on the outer surface of the conduit about the grasping end of the conduit.

5. An apparatus of claim 1 wherein the flexible sleeve is attached to the conduit by an adhesive.

6. An apparatus of claim 1 wherein the flexible sleeve is attached to conduit by a frictional interface fit between said flexible sleeve and said conduit.

7. An apparatus of claim 1 further including a finger retaining member mounted on the outer surface of the conduit adjacent the flexible sleeve to provide guidance during insertion of the apparatus in the body cavity.

8. An apparatus of claim 7 wherein the finger retaining member includes at least one generally circularly shaped finger-receiving portion.

9. An apparatus of claim 7 wherein the finger retaining member includes a tee shaped finger-receiving portion.

10. An apparatus of claim 7 wherein the finger retaining member is made from a soft resilient material.

11. A method of administering pills or parts thereof into a body cavity using a pill delivery apparatus having a flexible conduit and a slide wire disposed in said conduit and slidable therein, the method comprising the steps of:

loading a pill into a flexible sleeve attached to a delivery end of the flexible conduit to be inserted into the body cavity;

bending the flexible conduit into a desired shape to conform to the body cavity;

placing the flexible conduit in the body cavity;

pushing the slide wire having a ramming head element having a greater outer diameter than the inner diameter of the flexible conduit coupled to a ramming end of the slide wire toward the delivery end of the conduit to engage the pill with the ramming head element, unloading the pill into the body cavity; and removing the pill delivery apparatus from the body cavity.